(12) United States Patent
Beeckman et al.

(10) Patent No.: US 10,307,751 B2
(45) Date of Patent: Jun. 4, 2019

(54) APPARATUS AND METHOD FOR MIXING AND/OR MULLING A SAMPLE

(71) Applicants: Jean W. Beeckman, Columbia, MD (US); Natalie A. Fassbender, Nazareth, PA (US); Theodore E. Datz, Easton, PA (US); Chuansheng Bai, Phillipsburg, NJ (US); Adrienne J. Thornburg, Columbus, OH (US); Tilman W. Beutel, Neshanic Station, NJ (US)

(72) Inventors: Jean W. Beeckman, Columbia, MD (US); Natalie A. Fassbender, Nazareth, PA (US); Theodore E. Datz, Easton, PA (US); Chuansheng Bai, Phillipsburg, NJ (US); Adrienne J. Thornburg, Columbus, OH (US); Tilman W. Beutel, Neshanic Station, NJ (US)

(73) Assignee: EXXONMOBIL RESEARCH AND ENGINEERING COMPANY, Annandale, NJ (US)

(*) Notice: Subject to any disclaimer, the term of this patent is extended or adjusted under 35 U.S.C. 154(b) by 20 days.

(21) Appl. No.: 15/013,035

(22) Filed: Feb. 2, 2016

(65) Prior Publication Data
US 2018/0141033 A1    May 24, 2018

Related U.S. Application Data

(60) Provisional application No. 62/115,901, filed on Feb. 13, 2015.

(51) Int. Cl.
*B01J 37/04* (2006.01)
*B01J 37/00* (2006.01)
(Continued)

(52) U.S. Cl.
CPC ............. *B01J 37/04* (2013.01); *B01J 21/04* (2013.01); *B01J 35/023* (2013.01);
(Continued)

(58) Field of Classification Search
CPC ........................................................ B01J 37/04
(Continued)

(56) References Cited

U.S. PATENT DOCUMENTS

| | | | | |
|---|---|---|---|---|
| 165,192 | A * | 7/1875 | Warren | D21D 5/026 209/273 |
| 3,588,054 | A * | 6/1971 | Ljungberg et al. | B01F 11/0042 366/150.1 |
| 2004/0233779 | A1* | 11/2004 | Zambaux | B01F 11/0002 366/214 |

* cited by examiner

*Primary Examiner* — David L Sorkin
(74) *Attorney, Agent, or Firm* — Amanda K. Norwood

(57) ABSTRACT

Disclosed herein are an apparatus and a method for mixing and/or mulling a sample, the apparatus comprising at least one container made of a flexible material and containing a sample, means for holding the container, and means for impacting the container, wherein the means for holding and the means for impacting are movable relative to each other, and wherein the means for holding, the means for impacting, and the container are arranged such that the means for impacting and the container can repeatedly collide, whereby an energy of collision can be imparted to the sample, thereby mixing and/or mulling the sample. Also disclosed is an assembly for performing high throughput experiments including the apparatus for mixing and/or mulling a sample and an extruder configured to receive a sample weighing less than 100 grams.

13 Claims, 7 Drawing Sheets

(51) Int. Cl.
*B01J 35/02* (2006.01)
*B01J 21/04* (2006.01)
*B01J 35/10* (2006.01)
*C01B 33/26* (2006.01)

(52) U.S. Cl.
CPC ....... *B01J 35/1004* (2013.01); *B01J 35/1033* (2013.01); *B01J 37/0009* (2013.01); *B01J 2229/42* (2013.01); *C01B 33/2807* (2013.01); *C07C 2521/04* (2013.01)

(58) Field of Classification Search
USPC ................................ 366/209, 213, 214, 275
See application file for complete search history.

APPARATUS AND METHOD FOR MIXING AND/OR MULLING A SAMPLE

CROSS-REFERENCE TO RELATED APPLICATIONS

This application claims the benefit of provisional U.S. Ser. No. 62/115,901, filed Feb. 13, 2015, the entire contents of which are expressly incorporated by reference herein.

FIELD OF THE INVENTION

The invention relates to an apparatus and a method for mixing and/or mulling small amounts of samples, such as those encountered in high throughput experimentation, to form an extrudable paste of similar quality with the one obtained in pilot and industrial units.

BACKGROUND OF THE INVENTION

High throughput experiments (HTE) are extremely important in developing and improving processes for different application fields such as in the chemical or pharmaceutical industry. In particular HTE for zeolite synthesis, metals loading and reactor performance evaluation are required for developing and improving processes for the manufacturing of fuels, lubes and other advanced chemicals.

Up to now, efforts to evaluate new zeolites and catalysts derived therefrom have been limited because of the amount of starting material required to properly form extrudates. Catalyst extrusion, as conventionally practiced, requires at least 100 grams of material in order to properly prepare extrudates starting from powders. Typically, three steps are involved: 1) mixing of the dry powders, 2) mulling of the powders with added liquid and turning it into an extrudable paste, and 3) extrusion into the desired shape.

For small quantities of available catalyst material, usually dry pressing of the powders into pellets may be used, followed by breaking the pressed pellet and sizing it appropriately to accommodate into the reactor. The dry pressing at high pressure (about 10,000 psig or about 69 MPag) may compromise the catalyst pore structure and hence hamper reaction analysis and catalyst scalability. Also, dry pressing may hamper the interaction of the individual components in the mixing/mulling and extrusion processes. In addition, dry pressing is often limited in throughput because catalyst formation is ad-hoc, time consuming and labor intensive. Moreover, being a manual operation, it is also highly operator-dependent, which is an unwanted variability.

Therefore there is a need for a method that can overcome at least some of the above-mentioned drawbacks, by replacing the manual labor and the unwanted variability introduced by the operator and the variable quality of the formed catalyst support. Existing tools can only reliably process relatively high amounts of catalysts (e.g., amounts above 100 g), which are too large to consider processing samples in high throughput experiments. There is thus a need for a tool and a method that would allow properly mixing and/or mulling of small amounts of samples.

SUMMARY OF THE INVENTION

The purpose and the advantages of the present invention may be set forth in and apparent from the description that follows, as well as can be learned by practice of the invention. Additional advantages of the invention can be realized and attained by the methods and systems particularly pointed out in the written description and claims hereof, as well as from the appended drawings.

To achieve these and/or other advantages, and in accordance with one aspect of the invention, the present invention provides an apparatus for mixing and/or mulling a sample. The apparatus can comprise at least one container made of a flexible/elastic material, which can be suitable for containing a sample weighing less than 100 g, for example less than about 75 g, less than about 50 g, less than about 20 g, or less than about 10 g. The apparatus can comprise means for holding the at least one container and means for impacting the at least one container, wherein the means for holding and the means for impacting can advantageously be movable relative to each other, and wherein the means for holding, the means for impacting and the at least one container can be adapted/arranged such that, when the means for holding and the means for impacting are caused to move relative to each other, the means for impacting and the at least one container can repeatedly collide. The energy of collision can thus be imparted to the sample contained in the at least one container, thereby mixing and/or mulling the sample, for instance to form an extrudable paste.

In embodiments, the means for holding can be arranged to move (e.g., to rotate) and the means for impacting can be stationary, or alternately both the means for holding and the means for impacting can be arranged to move (e.g., to rotate), such that the means for impacting and the at least one container can repeatedly collide. In alternate embodiments, the means for impacting can be arranged to move (e.g., to rotate) and the means for holding can be stationary.

The means for holding may comprise at least one disk mounted on a rotatable shaft. The disk may comprise a plurality of mounting positions, each mounting position being adapted and/or adaptable to hold a container. Alternately, the means for holding may comprise at least one arm mounted on a rotatable shaft, which arm can comprise, at its unmounted (free) end, a mounting position arranged to hold a container. The means for impacting can comprise at least one arm mounted on a rotatable shaft.

In certain embodiments, the flexible material of the container can be substantially impermeable to any liquid present in the sample, thereby effectively sealing the sample. Alternately, the flexible material may be permeable to fluids, thereby effectively exposing the sample to, e.g., gases/vapors, during the mixing and/or mulling process.

In some embodiments, the apparatus may comprise means for heating/cooling and/or means for irradiating the at least one container containing the sample. Additionally or alternately, the apparatus may comprise means for supplying an additional fluid to an enclosure of the apparatus containing the at least one container.

Another aspect of the present invention includes a method for mixing and/or mulling a sample. A sample weighing less than 100 grams (for example less than about 75 grams, less than about 50 grams, less than about 20 grams, or less than about 10 grams) can be introduced into the at least one container made of a flexible material. The method can comprise mounting the container on a means for holding and providing a means for impacting. The means for holding and/or the means for impacting can (be adapted to) move relative to each other such that the at least one container and the means for impacting can repeatedly collide. Such repeated collisions can advantageously impart an energy of collision to the sample(s) contained in the at least one container, thereby mixing and/or mulling the sample, e.g., to form an extrudable paste.

In embodiments, the method can comprise moving (e.g., rotating) the means for holding, while the means for impacting can remain stationary, or alternately moving (e.g., rotating) both the means for holding and the means for impacting, such that the means for impacting and the at least one container can repeatedly collide. In alternate embodiments, the method can comprise moving (e.g., rotating) the means for impacting, while the means for holding can remain stationary.

The sample can typically comprise a solid material. The solid material may include or be one or more of a catalyst, a binder, a pharmaceutical compound, and a combination thereof. In some embodiments, the sample may additionally comprise one or more of a liquid, an additive, a metal, an extrusion aid, a mulling aid, and a combination thereof.

The method can comprise exposing the sample contained in the at least one container to a heat source, a photon source, a fluid, or any combination thereof, either before or while the at least one container and the means for impacting are in the process of repeatedly colliding.

Still another aspect of the present invention can include a method of extruding a sample comprising mixing and/or mulling a sample, such as according to any of the embodiments disclosed herein, thereby forming an extrudable paste, then feeding the extrudable paste into an extruder adapted to receive relatively small amounts of sample (e.g., weighing less than 100 grams, less than about 75 grams, less than about 50 grams, less than about 20 grams, or less than about 10 grams).

Yet another aspect of the present invention can include an assembly for performing high throughput experiments comprising an apparatus for mixing and/or mulling a sample and an extruder configured to receive a sample weighing less than 100 grams (for example less than about 75 grams, less than about 50 grams, less than about 20 grams, or less than about 10 grams).

In embodiments of the several aspects of the invention, the extruder can include or be an apparatus comprising a die set that can include a die body, a base, a plunger, means for exerting pressure on the sample, and an orifice above the base, wherein the apparatus is configured such that, upon increasing pressure on the die set, a single extrudate can emerge from the orifice. In additional or alternate embodiments, the extruder can include or be a laboratory extrusion tool comprising a plunger, a sample holder, an inner chamber, an extrusion die, and a die holder, configured such that, upon loading the sample and applying/increasing pressure, the sample can be extruded through the extrusion die.

These and other features of the present invention should become apparent from the following detailed description of preferred embodiments, which, taken in conjunction with the accompanying drawings, can illustrate by way of example principles of the present invention.

BRIEF DESCRIPTION OF THE DRAWINGS

While the present disclosure is susceptible to various modifications and alternative forms, specific examples thereof have been shown in the drawings and are herein described in detail. It should be understood, however, that the description herein of specific embodiments is not intended to limit the disclosure to the particular forms disclosed herein and/or as recited in the appended claims, but, on the contrary, this disclosure is intended to cover all reasonable modifications and equivalents. It should also be understood that the drawings are not necessarily to scale, emphasis instead being placed upon clearly illustrating principles of exemplary embodiments of the present invention. Indeed, certain dimensions may be exaggerated to help visually convey such principles.

DETAILED DESCRIPTION OF THE EMBODIMENTS

Figure 1:
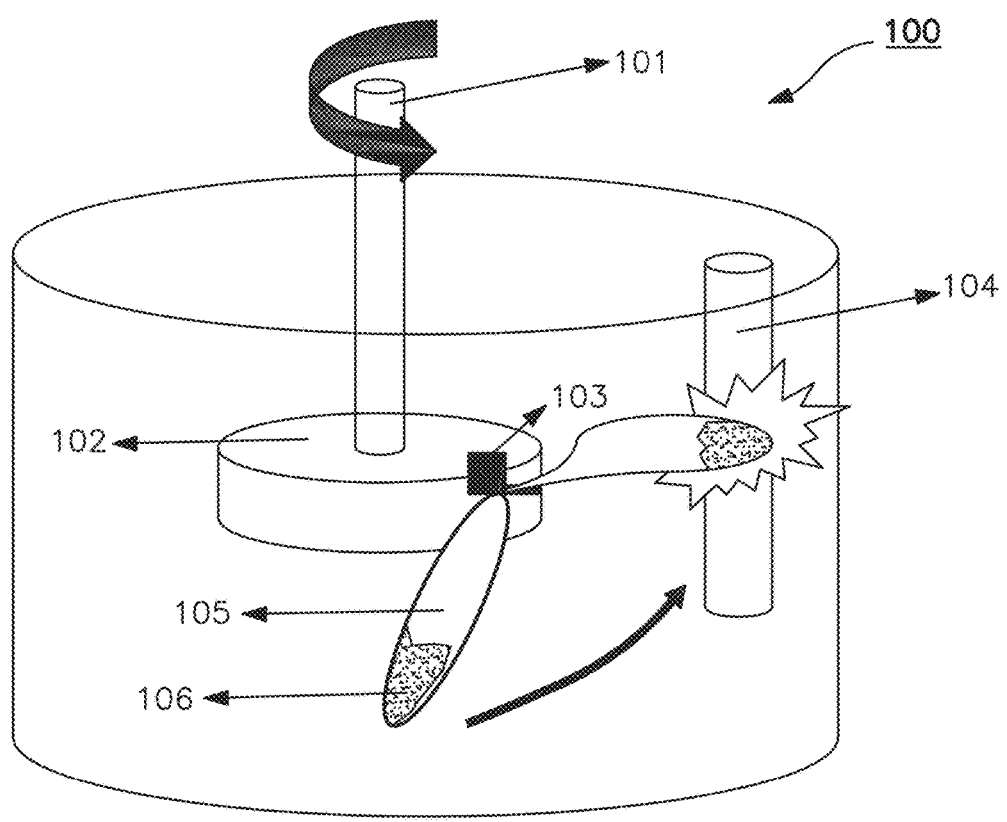
FIG. 1 shows schematically the apparatus for mixing and/or mulling a sample according to embodiments of the invention.

In the following detailed description, the specific embodiments of the present invention are described in connection with some exemplary and some preferred embodiments. However, to the extent that the following description is specific to a particular embodiment or a particular use of the present invention, this is intended to be for exemplary purposes only and simply to provide a description of the exemplary embodiments. Accordingly, the invention is not meant to be unduly limited to the specific embodiments described below, but rather to include all reasonable alternatives, modifications, and equivalents falling within the true spirit and scope of the appended claims.

In an aspect, the invention relates to an apparatus for mixing and/or mulling a sample suitable to process relatively smaller quantities/gram amounts of a sample thereby forming a mixture, which may also be described as an extrudable paste, having substantially similar properties as mixtures obtained using a conventional industrial tool adapted to process relatively larger quantities.

Other, potentially related aspects involve a method for mixing and/or mulling relatively smaller quantities, e.g., gram amounts, of a sample thereby forming a mixture or an extrudable paste having substantially similar properties as mixtures obtained industrially (typically used to process relatively larger sample quantities).

Throughout the disclosure, when referring to gram amounts or relatively smaller quantities of sample, it is meant an amount weighing less than 100 grams (for example less than about 75 grams, less than about 50 grams, less than about 20 grams, less than about 10 grams, less than about 5 grams, or less than about 1 gram), and optionally but typically at least a fraction of a gram (e.g., at least about 0.01 grams, at least about 0.05 grams, at least about 0.1 grams, at least about 0.2 grams, at least about 0.3 grams, at least about 0.4 grams, or at least about 0.5 grams). High throughput experiments involving higher total amounts of samples are possible, since multiple samples can be processed at the same time in multiple containers (mounted on the same apparatus), without cross contamination.

The apparatuses and the methods according to the invention can, in some embodiments, include forming a mixture or a paste from gram amounts of sample within a similar processing time as industrial tools typically used to process relatively larger sample quantities. The apparatuses and the methods according to the invention can advantageously result in improved sample quality, e.g., by diminishing substantially the contamination risk and/or by improving control of the composition in high throughput experiments.

Advantageously, the apparatuses and the methods according to the invention can replace dry pressing and manual labor, such as currently used in the preparation of gram amounts of sample.

Apparatuses according to the invention can advantageously be used to process multiple samples at the same time, while avoiding intermixing and contamination, such that sample purity and sample composition can be safeguarded. Therefore, the apparatuses and methods according to the invention can be suitable for high throughput experiments by handling such multiple samples, particularly when each of the samples is present in relatively smaller quantities. Various applications can be envisaged in the chemical and pharmaceutical industries, such as preparation of catalysts and/or pharmaceutical mixtures, as well as in other industries.

The extrudates obtained from pastes prepared according to the invention can be evaluated in comparison to reference samples. Such reference samples can be processed either in a mixing and/or mulling pilot tool or in an industrial tool typically used to process relatively larger sample quantities. Pore volume, surface area, crush strength, and morphology of extrudates obtained using methods according to the invention can advantageously be very similar to the reference samples obtained by conventional means (indeed, in some cases, indistinguishable). Advantageously, extrudable pastes prepared according to the invention can comprise similar percentages of solids and can have about the same processing time as industrially prepared pastes.

Apparatuses according to the invention can include at least one container (e.g., made of a flexible material), means for holding the at least one container, and means for impacting the at least one container. The at least one container can advantageously be suitable for containing a sample. The means for holding and the means for impacting can be movable (mobile) relative to each other. The means for holding, the means for impacting, and the at least one container can be arranged/adapted such that, when the means for holding and the means for impacting are moving relative to each other, the means for impacting and the at least one container can repeatedly collide, whereby an energy of collision can be imparted to the sample contained in the at least one container, thereby mixing and/or mulling the sample, such as to form an extrudable paste.

An extrudable paste, as used herein, should be understood to refer to a paste that can be extruded into typically-sized extrudates of varying shapes and sizes, e.g., under extruder pressures from about 300 psig to about 2000 psig (from about 2.1 MPag to about 13.8 MPag).

The energy of collision that can be imparted to the sample, thereby effectuating the mixing and/or mulling process, can gradually proceed by particle-particle interactions in the container, for example, without any grinding media being required to assist the process.

The means for impacting and the at least one container can repeatedly collide, particularly when the relative movement between the means for holding and the means for impacting occurs as a repetitive movement, such as rotation or oscillation. The repetitive movement may happen with a constant and/or variable frequency. The frequency of collisions can be modified by varying the speed/frequency of the movable (e.g., rotatable) parts. Therefore, the method can, in this way, be operator independent and, if desired, can eliminate unwanted variability and/or errors in sample preparation/testing.

Arranging (configuring) the means for holding, the means for impacting, and the at least one container can be performed by adapting a dimension and/or a relative position of any of the means for holding, the means for impacting, and the at least one container, with respect to each other.

Adapting a dimension means, for example, adapting at least one of a length, width, or height of any of the means for holding, the means for impacting, and the at least one container. Adapting the length/width/height of the means for holding may optionally include adapting a length/width/height of any parts (components) of the means for holding, such as the means for fixing at the mounting position.

Adapting a relative position of any of the means for holding, the means for impacting, and the at least one container with respect to each other can mean any one or more of the following: varying a distance and/or an orientation (angle), e.g., between the means for holding and the means for impacting; varying a distance and/or an orientation between the means for impacting and the container; and varying a distance and/or an orientation between the means for holding and the container.

The mixing and/or mulling process of the invention can advantageously occur on the same processing time scale as the corresponding process in industrial tools, which can range typically from a few minutes (e.g., about 5 minutes) to about 1 hour. This can be an important advantage, because processing times which are too long or too short can lead to increased temperatures in the paste (e.g., up to about 50° C. or up to about 60° C.) or to poor paste formation, respectively. Increased temperature of the paste may trigger moisture loss and may therefore change the extrudate composition undesirably. Poor paste formation can lead to liquid dripping off during extrusion and thereby to undesirable changes in the extrudate composition.

Furthermore, by producing a mixture or extrudable paste of a similar quality as industrial mixtures, the invention can enable performing the extrusion of the relatively small quantities of sample at pressures comparable with those used in industrial extruders, e.g., from about 500 psig (about 3.4 MPag) to about 1500 psi (about 10.3 MPag). Currently, dry pressing can be typically employed for relatively small amounts of sample, which can generally correspond to pressures of at least about 10000 psig (about 69 MPag).

The means for holding may comprise one or more holders. The means for impacting may comprise one or more impacting units.

In certain embodiments, the means for holding can be arranged to perform a repetitive movement, e.g., such as a rotation and/or an oscillation, while the means for impacting can be stationary/fixed within the frame of the apparatus. In particular, the means for holding can be arranged to rotate and the means for impacting can be stationary (fixed). For instance, the means for impacting can include or be a fixed pole, e.g., substantially parallel to a rotation axis of the means for holding.

In other embodiments, the means for holding and the means for impacting can both be arranged to perform a repetitive movement, such as rotation, their movement (rotation) amplitude(s)/frequency(ies) capable of being adapted such that the means for impacting and the at least one container can repeatedly collide.

In the embodiments where both the means for holding and the container are adapted to perform a rotation movement, a total weight of the at least one container containing the sample and the means for holding can be uniformly distributed around the rotation axis, e.g., in order to balance the whole rotating assembly, thereby enabling a stable rotational movement.

In some embodiments, the means for holding may comprise at least one disk mounted on a rotatable shaft, which can advantageously be actioned by a motor. In such embodiments, the at least one disk can comprise a plurality of mounting positions, each mounting position being arranged to hold at least one container. Advantageously, when the means for holding and the container are rotated, centrifugal force can push/maintain the sample together at the bottom of the container.

The mounting position may comprise fixing means configured to hold the container. For example, the mounting position can be a mounting slot. A plurality of disks can be mounted on the rotatable shaft at different heights, potentially increasing the number of the samples that can be processed simultaneously. The distance between any two adjacent disks can be adapted to allow easy accessibility to the containers.

Additionally or alternatively, the means for holding may comprise at least one arm mounted on a rotatable shaft, which can advantageously be actioned by a motor. In such embodiments, the at least one arm can comprise, at its unmounted (free) end, a mounting position, e.g., such as a mounting slot arranged to hold at least one container.

In certain embodiments, the means for impacting can be arranged/adapted to allow motion, and the means for holding can be stationary/fixed to a frame (or a case) of an apparatus (e.g., such as an apparatus according to the invention), such that the means for impacting can impact (collides with) the at least one container. For example, the means for impacting can rotate around a rotation axis, while the means for holding can be stationary, e.g., held at a distance from the rotation axis. Additionally or alternatively, the at least one container can be positioned (at a height), such that the means for impacting can repeatedly impact (collide with) the at least one container. For example, the means for impacting may comprise at least one arm mounted on a rotatable shaft, which can advantageously be actioned by a motor.

The apparatus may comprise a protection case at least partially encapsulating the means for holding, the means for impacting, and/or the at least one container. The protection case can be designed to protect at least the portion of the apparatus surrounding the impact area, where the collision between the means for impacting and the container can take place, allowing for safe processing. The protection case can optionally have with a window for operator inspection.

The apparatus may further comprise means for heating/cooling and/or means for irradiating the container (and thus the sample contained therein). Non-limiting examples thereof can include one of more of a heating element, an infrared (IR) lamp, an ultraviolet (UV) lamp, a source of microwaves and/or radio-waves with a suitable frequency, any equivalents recognized by those skilled in the art, and combinations thereof.

Additionally or alternatively, the apparatus may comprise an enclosure (e.g., a reaction chamber), which can include at least the container and the impact area. Advantageously, the enclosure can be contained within the protection case. The enclosure may comprise means for supplying/evacuating a fluid, such as reactive and/or inert gases/vapors.

Additionally or alternatively, the apparatus may comprise means to control the environment within the enclosure (e.g., reaction chamber), such as means to control the temperature, the humidity, and/or the composition of the atmosphere in the enclosure.

The at least one container can advantageously be made of a flexible material such as suitable for containing a sample weighing less than 100 grams (e.g., less than about 75 grams, less than about 50 grams, less than about 20 grams, less than about 10 grams, less than about 5 grams, or less than about 1 gram).

The flexible material can advantageously include or be a material having elastic properties that a) can be stable when in contact with the mixture inside the container for a time long enough to perform the mixing/mulling, and b) can withstand the repeated impacts to accomplish the mixing/mulling (often at least several thousands of impacts and, in some cases, up to about 100,000 impacts). The flexible material may include one or more layers made of the same or of different materials. Due to the flexibility (elasticity) of the material, the energy of impact upon collision can be (significantly) transmitted integrally to the sample, instead of being primarily absorbed by the container walls. In some embodiments, one such layers can be a liner and/or a coating. Non limiting examples of suitable flexible materials can include rubbers of various compositions, optionally with a protective coating/lining.

The flexible material of the container can functionally limit/prevent the (each) sample from caking up on the container walls, such that no grinding material may be needed. Therefore, this can enable a sample recovery of about 100%, as the sample(s) can be transferred from the container into an extrusion die holder with relative ease. Additionally or alternatively, the flexible material may include reinforcing fibers, for instance to strengthen its mechanical properties without substantially reducing its elastic properties.

In a particular embodiment, the container can be a pouch made of a flexible material, having an oblong shape relatively easy to fill with solids, for example, using a funnel, and wherein liquids can be introduced such as by using a pipette/syringe.

Depending on the application field, the flexible material can be relatively/substantially impermeable to water and/or other fluids, thereby allowing a substantially hermetic seal, or can alternatively allow some/substantial movement of fluids.

Hermetically sealed containers typically do not allow significant moisture evaporation and/or contamination by the ambient atmosphere and therefore can offer heightened composition control of the mixture. Moreover, such sealed containers can leave more flexibility to the operator to plan the extrusion timing. The duration to produce an extrudable paste with the methods disclosed herein can vary, for instance with the composition of the sample(s), but can advantageously be conducted over similar duration as industrially prepared pastes.

Additionally or alternatively, somewhat permeable containers can allow interaction between the sample(s) and the ambient atmosphere during processing. Combining the use of permeable containers with a controlled environment in the chamber of the mixing and/or mulling apparatus can enable chemical reactions to occur in the container simultaneously with mixing and/or mulling. For example, by providing a fluid (e.g., a gas) that can react with some/all of the sample(s) in the container, further reactions and/or enhanced reactions can take place during the mixing and/or mulling stage(s).

Further additionally or alternatively, the sample can be exposed to a heating element and/or to a source of photons (radiation source) prior to or during the mixing and/or mulling process for a certain time, thereby providing additional energy to the sample(s). The energy provided can be used to speed up the mixing and/or mulling process and/or to trigger chemical/photo-induced transformations in the sample(s).

In embodiments wherein exposure to a heating element may be desired, the flexible material of the container can advantageously be sealed to prevent substantial moisture loss. Contrary to conventional mixing/mullers, where heating the mixture is typically avoided to prevent liquid loss, the methods disclosed herein can allow mixing and/or mulling at temperatures above room temperature (e.g., at about 40° C. to about 60° C.) without a significant loss of moisture (e.g., less than 5% moisture loss, less than 1% moisture loss, less than 0.1% moisture loss, or no measurable moisture loss).

In embodiments where exposure to a source of photons (e.g., UV lamp) may be desired, the flexible material of the container can advantageously be highly (e.g., at least 75%, at least 85%, at least 90%, or at least 95%) transparent to the wavelength range employed.

Methods for mixing and/or mulling samples according to the invention can simply involve use of the apparatuses described herein. In one such method for mixing and/or mulling a sample, the method can comprise: (a) introducing a sample into at least one container made of a flexible material; (b) mounting the at least one container on a means for holding; (c) providing a means for impacting; (d) moving the means for holding or the means for impacting relative to each other, such that the at least one container and the means for impacting can repeatedly collide, whereby an energy of collision can be imparted to the sample contained in the at least one container, thereby mixing and/or mulling the sample. Through mixing and/or mulling the sample can advantageously be transformed into an extrudable paste.

In certain embodiments, the methods can comprise rotating the means for holding, while the means for impacting is stationary/fixed to a frame (case) of the apparatus.

Additionally or alternatively, both the means for holding and the means for impacting can rotate, for instance in opposite directions, with rotation amplitude(s)/frequency(ies) such that the means for impacting and the at least one container can repeatedly collide.

Further additionally or alternately, the methods can comprise rotating the means for impacting, while the means for holding is stationary/fixed to a frame (case) of the apparatus, such that the means for impacting and the at least one container can repeatedly collide.

The (each) sample can, in some embodiments, comprise a solid material and, optionally, a liquid (which can be contained, e.g., as adsorbed liquid, among/within the solid material). The solid material may include or be one or more of a catalyst, a binder, carbon powder, a pharmaceutical compound, and a combination thereof.

Further, the (each) sample can comprise one or more of a liquid, an extrusion aid, an additive, a mulling aid, or a combination thereof. The liquids can be provided in the container before mixing and/or mulling is started, and/or can be added during the mixing and/or mulling process, to obtain a desired composition and/or mixture consistency.

Methods according to the invention can further comprise adding liquids and/or additives to a/the/each sample during the mixing and/or mulling process. After mixing and/or mulling for a time interval, the relative movement can be stopped, the containers can be opened, and the liquids and/or additives can be added, e.g., using a syringe/pipette. Additionally or alternatively, liquids can be added to an unopened container (e.g., by a syringe piercing the container to add a liquid), after which the containers can be closed again to resume the mixing and/or mulling process.

Any liquid compatible with the flexible container material can be added, such as, depending on the type of flexible material used, water, an inorganic acid (e.g., nitric acid), an organic acid (e.g., acetic acid), a base, an extrusion aid, a pharmaceutical additive, or a combination thereof. An extrusion aid can typically include an organic material capable of facilitating extrusion.

Additives such as metals, metal compounds, metal solutions, and/or pharmaceutical additives can be provided before the mixing and/or mulling is started and/or can be added during the mixing and/or mulling process. Non-limiting examples of metals comprising and/or included in such additives can include, but are not necessarily limited to, Pt, Pd, Ir, Co, Mo, W, Ti, Zr, and combinations thereof.

A mulling aid may comprise a material suitable to assist the mulling process, sometimes when the/each sample amount is very small, e.g., about 0.5 grams or less. Such a mulling aid material may comprise small spheres (e.g., spheres having a diameter of about ¼ inch (~6.3 mm) or less) that can be made of a soft flexible material such as rubber. The mulling aid can be separated from the extrudable paste, typically before feeding the paste into the extruder.

Upon processing the sample by methods according to the invention, an extrudable paste can be obtained, which can be fed directly into an extruder adapted to process relatively small amounts of paste, as described in further detail herein.

FIG. 1 shows schematically an apparatus for mixing and/or mulling (100) according to one embodiment of the invention, comprising a spinning disk (102) mounted on a vertical shaft (101) rotating around a vertical axis with a controlled speed (e.g., about 600 rpm).

In this particular Fig., the disk has 6 mounting slots (103), each of the slots holding a pouch/sock (105) made of rubber. Each pouch is capable of holding gram amounts of a sample (106). While the pouches can spin together with the disk, the sample can be pushed by the centrifugal force at the bottom of the pouches.

In a particular embodiment, all the components used to make the extrudable paste can be introduced into the rubber pouches before mixing and/or mulling begins. The length of the pouches can be adjusted such that the spinning pouches (spinning nearly horizontally) can hit approximately once per revolution a smooth metallic pole (104) fixed within the apparatus frame.

In a particular example of such an embodiment, the pouches had a length of about 6 inches (~15 cm) and a diameter of about 1 inch (~2.5 cm). At a rotation speed of about 600 rpm, the pouches were spun to hit the metallic pole about 10 times per second. The energy of collision (impact) imparted to the/each sample in the pouch thereby effected the mixing and/or mulling of the/each sample. The samples were spun for minutes or longer, until they acquired the desired consistency. Readiness of the mixture, in some situations, can be judged by the formation of small spheres of material about ⅛ inch (~3.2 mm) in size. An adequate mixing of powders can be obtained after about 30 seconds, while mulling can typically require longer time intervals, as noted in the Examples below.

When a sample containing powder(s) and, optionally, liquid(s) is processed, that sample can go through different stages: first, after about 10-60 seconds, an early mix can be formed; then, after about 2-10 minutes, an advanced mixture/mull agglomeration can be formed; and, finally, an extrudable paste can be formed after about 10-30 minutes.

Figure 2A:
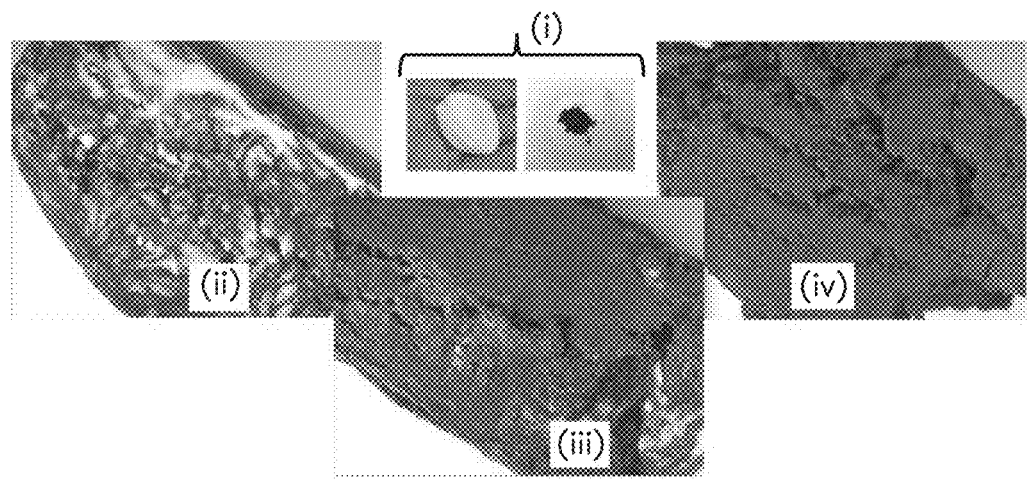
FIG. 2A (views (i), ((ii), (iii) and (iv))
Figure 2B:
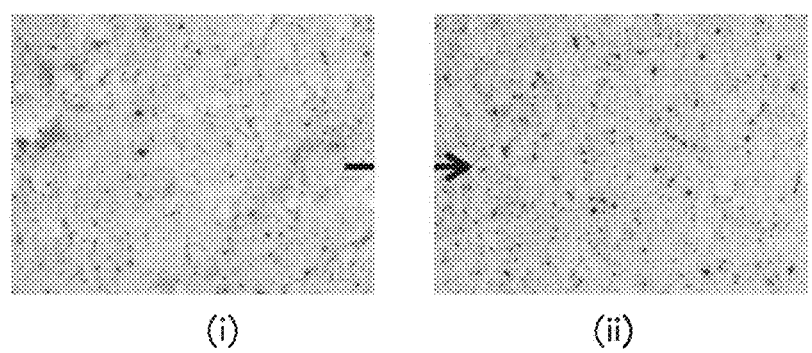
FIG. 2B (views (i) and (ii)); and, FIG. 2C represent microscope images of carbon powder and carbon fiber containing mixtures prepared according to embodiments of the invention.
Figure 2C:
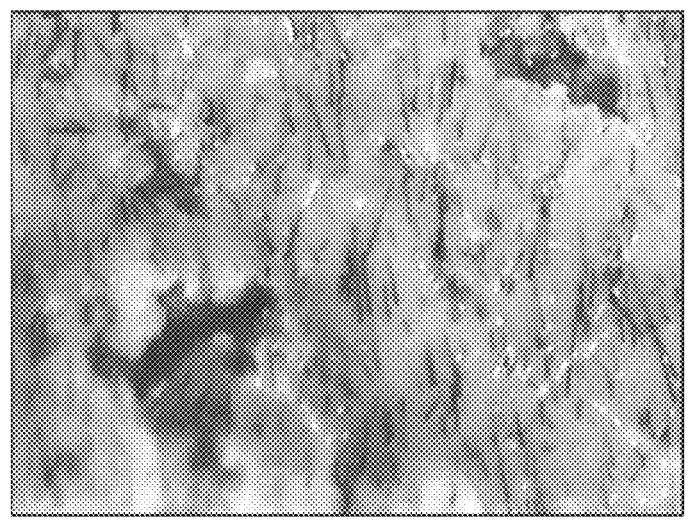

FIG. 2A (views (i), ((ii), (iii) and (iv)); FIG. 2B (views (i) and (ii)); and, FIG. 2C illustrate carbon powder- and carbon fiber-containing mixtures prepared according to methods of the invention, each having a relatively high degree of long and short range mixing effectiveness after wet and dry mixing.

The experiments in FIG. 2A (views (i), (ii), (iii) and (iv)) have been performed with a wet mull mixture obtained from a previous mixing/mulling experiment and carbon powder, as initial components (see FIG. 2A (view (i))). FIG. 2A (views (ii), (iii) and (iv) show the progressive mixing with increasing processing time: view (ii) ~30 seconds; view (iii) ~1 minute; and view (iv) ~3 minutes. Since the carbon powder was added to a wet mull mix previously prepared, the experiment is offered to show the mixing and/or mulling process continuing even after an initial paste (or wet mull mix) was formed. The addition of liquids, additives, and/or extrusion can thus be done at any stage in the mixing and/or mulling process.

The experiments in FIG. 2B (views (i) and (ii)) were performed by dry mixing components at about 600 rpm. The pictures were taken after view (i) ~30 seconds and view (ii) ~3 minutes. FIG. 2C shows long range wet carbon fiber mixing after ~30 seconds.

A small scale catalyst preparation facility for performing high throughput experiments may integrate a mixing and/or mulling apparatus with an extruder suitable to process relatively small quantities of sample for forming extrudates having similar properties with those produced by industrial/pilot facilities. Industrial and pilot extruders are typically not suitable, because they typically require relatively large amounts of paste to be processed in order to function properly. Therefore, in an aspect of the invention, laboratory scale extruders can be suitably used for forming extrudates from the paste obtained with the mixing and/or mulling apparatuses/methods described herein. Extrudates obtained with the laboratory scale extruders were evaluated against industrial and/or pilot scale extrudates, by comparing their physical and chemical properties. The Examples below may provide more details.

Additionally or alternately, the invention can further relate to one or more of the following embodiments.

Embodiment 1

An apparatus for mixing and/or mulling a sample comprising: at least one container made of a flexible material, the at least one container being suitable for containing a sample; means for holding the at least one container; and means for impacting the at least one container, wherein the means for holding and the means for impacting are movable relative to each other, wherein the means for holding, the means for impacting, and the at least one container are arranged such that, when the means for holding and the means for impacting are moving relative to each other, the means for impacting and the at least one container repeatedly collide, whereby an energy of collision is imparted to the sample contained in the at least one container, thereby mixing and/or mulling the sample.

Embodiment 2

The apparatus according to embodiment 1, wherein arranging the means for holding, the means for impacting, and the at least one container is performed by adapting a dimension and/or a relative position of any of the means for holding, the means for impacting, and the at least one container with respect to each other.

Embodiment 3

The apparatus according to embodiment 1, wherein the means for holding is arranged to rotate and the means for impacting is stationary, or wherein both the means for holding and the means for impacting are arranged to rotate, such that the means for impacting and the at least one container repeatedly collide.

Embodiment 4

The apparatus according to any one of the preceding embodiments, wherein the means for impacting is arranged to rotate and the means for holding is stationary.

Embodiment 5

The apparatus according to any one of the preceding embodiments, wherein the means for holding comprise at least one disk mounted on a rotatable shaft, the at least one disk comprising a plurality of mounting positions, each mounting position being adapted to hold a container.

Embodiment 6

The apparatus according to any one of embodiments 1-4, wherein the means for holding comprise at least one arm mounted on a rotatable shaft, the at least one arm comprising at its unmounted end a mounting position adapted to hold a container.

Embodiment 7

The apparatus according to any one of embodiments 4-6, wherein the means for impacting comprise at least one arm mounted on a rotatable shaft.

Embodiment 8

The apparatus according to any one of the preceding embodiments, wherein the at least one container is suitable for containing a sample weighing less than 100 grams (e.g., less than about 75 grams, less than about 50 grams, less than about 20 grams, less than about 10 grams, less than about 5 grams, or less than about 1 gram).

Embodiment 9

The apparatus according to any one of the preceding embodiments, wherein the flexible material of the container is impermeable to any liquid contained in and/or formed by the sample.

Embodiment 10

The apparatus according to any one of the preceding embodiments, further comprising at least one of means for heating and means for irradiating the at least one container.

Embodiment 11

The apparatus according to any one of the preceding embodiments, further comprising means for supplying an additional fluid to an enclosure of the apparatus containing the at least one container.

Embodiment 12

A method for mixing and/or mulling a sample, comprising: introducing a sample in at least one container made of a flexible material; mounting the at least one container on a means for holding; providing a means for impacting; and moving the means for holding and/or the means for impacting relative to each other such that the at least one container and the means for impacting repeatedly collide, whereby an energy of collision is imparted to the sample contained in the at least one container thereby mixing and/or mulling the sample.

Embodiment 13

The method according to embodiment 12, comprising rotating the means for holding while the means for impacting is stationary, or rotating both the means for holding and the means for impacting, such that the means for impacting and the at least one container repeatedly collide.

Embodiment 14

The method according to embodiment 12, comprising rotating the means for impacting, while the means for holding is stationary.

Embodiment 15

The method according to any one of embodiments 12-14, further comprising exposing the sample contained in the at least one container to a heat source, a photon source, a fluid, or any combination thereof, either before or while the at least one container and the means for impacting are repeatedly colliding.

Embodiment 16

The method according to any one of embodiments 12-15, wherein the sample comprises a solid material, which can comprise a catalyst, a pharmaceutical compound, or a combination thereof, and optionally wherein the sample further comprises one or more of a liquid, an additive, a metal, an extrusion aid, a mulling aid, and a combination thereof.

Embodiment 17

An assembly for performing high throughput experiments comprising: an apparatus for mixing and/or mulling a sample according to any one of claims 1-11; and an extruder configured to receive a sample weighing less than 100 grams (e.g., less than about 75 grams, less than about 50 grams, less than about 20 grams, less than about 10 grams, less than about 5 grams, or less than about 1 gram).

Embodiment 18

The assembly according to embodiment 17, wherein the extruder is a single extrudate apparatus comprising a die body, a base, a plunger, means for exerting pressure on the sample, and an orifice above the base, configured such that, upon loading the sample and increasing pressure, a single extrudate emanates from the orifice, or wherein the extruder is a laboratory extrusion tool comprising a plunger, a sample holder, an inner chamber, an extrusion die, and a die holder, configured such that, upon loading the sample and increasing pressure, the sample is extruded through the extrusion die.

Embodiment 19

A method for extruding a sample, comprising: mixing and/or mulling a sample using the method according to any one of embodiments 12-16, thereby forming an extrudable paste; and feeding the extrudable paste into an extruder configured to receive a sample weighing less than 100 grams (e.g., less than about 75 grams, less than about 50 grams, less than about 20 grams, less than about 10 grams, less than about 5 grams, or less than about 1 gram).

EXAMPLES

Example 1: Laboratory Extrusion Tool

Figure 3A:
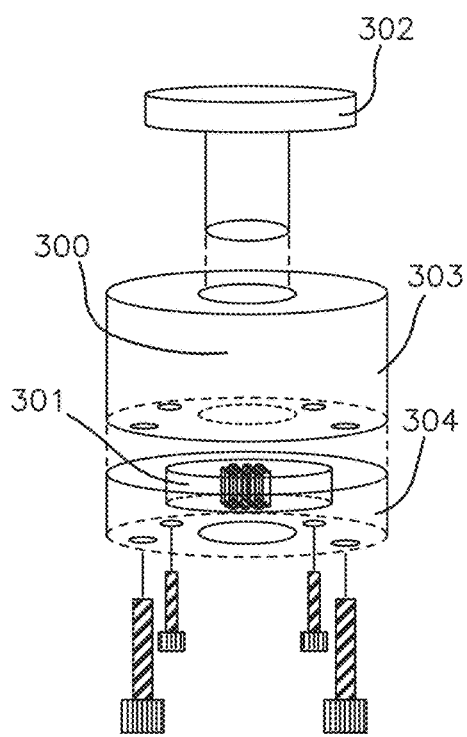
FIG. 3 (views A and B) show schematically a laboratory extrusion tool configured to be used with the mixing and mulling device.
Figure 3B:
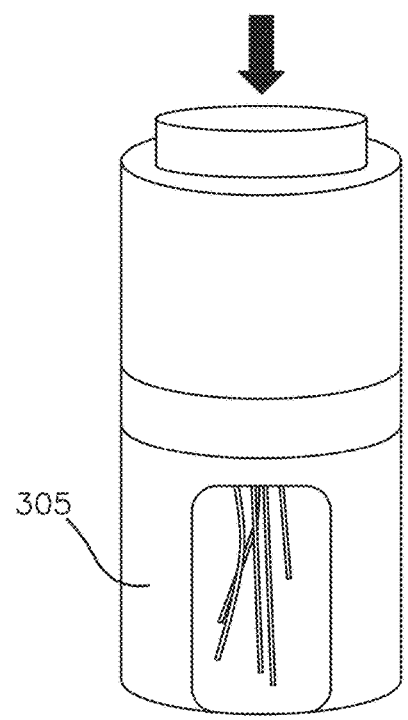

FIG. 3 (views A and B) show schematically a laboratory extrusion tool, referred to further as the HTME tool, which comprised a plunger (302), a sample holder (303), an inner chamber (300), an extrusion die (301), a die holder (304), and a stand (305). Components were secured together by screws. A sample (wet mull obtained with the mixing and/or mulling apparatus) was loaded into chamber. Thereafter a clamping force was applied top-down, and the wet mull was extruded through the die and recovered under the die holder in the stand.

In one experiment, the extruder accepted commercial die inserts and was particularly convenient for quantities of about 5 grams or slightly larger, for example between about 5 grams and about 10 grams.

In another experiment, the extruder had a custom designed die with a ~13 mm piston, referred further as the HTME 13 mm. It worked effectively with quantities of less than ~5 grams (e.g., from about 1 gram to 3 grams) and at pressures close to those used in commercial extruders (e.g., about 1000 psig or ~6.9 MPag). The extrudates obtained had a size of ~1.58 mm (~$\frac{1}{16}$ inch) with cylindrical and/or quadrulobal shapes. In both experiments, the extruders were characterized by a high sample recovery (about 80%).

Figure 4:
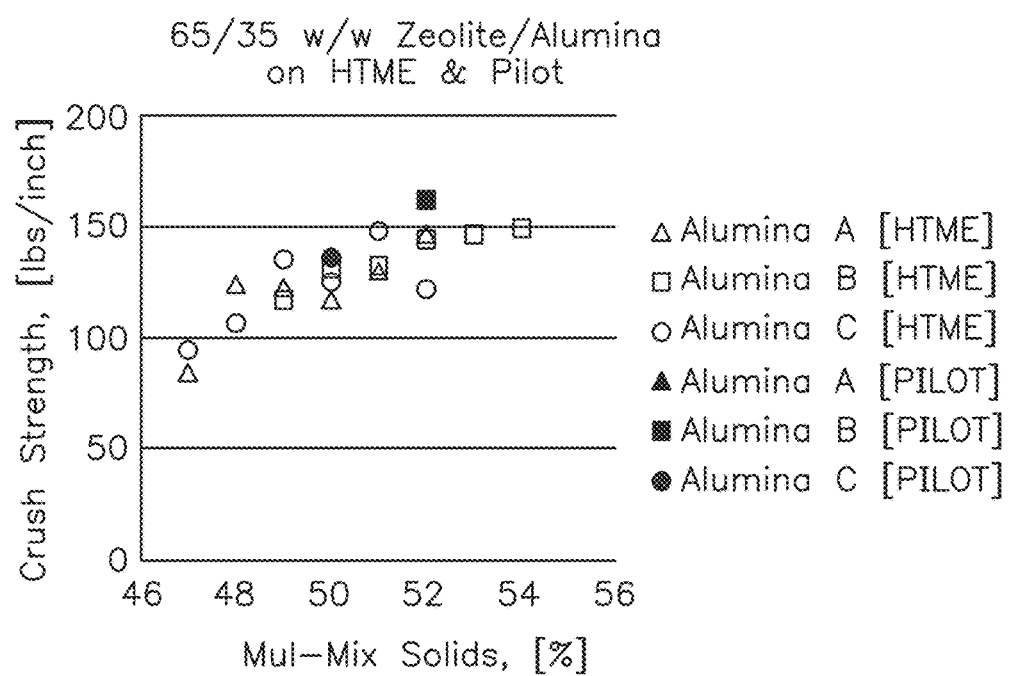
FIG. 4 represents the crush strength (lbs/in) for samples prepared according to the method of the invention in high throughput experiments assembly and with a ~2-inch PILOT extruder from ~65/~35 zeolite/alumina, for different types of alumina, as function of the percentage of solids.

FIG. 4 represents the crush strength (in lbs/inch) for different samples mixed, mulled, and then extruded according to a method of the invention with the laboratory extrusion tool (HTME, open symbols). Samples with the same composition were extruded with a ~2-inch (~5.1-cm) pilot extruder (PILOT, closed symbols), for comparison. The samples were prepared from ~65 parts zeolite and ~35 parts alumina, with different alumina binders and different percentages of solids (wt %) in the mixture. The crush strength of the samples varied from about 100 lbs/inch (~18 kgf/cm) to about 150 lbs/inch (~27 kgf/cm), depending on the solid content and the sample.

Further, the properties of extrudates prepared with the HTME extrusion tool were compared with the properties of extrudates obtained with the ~2-inch (~5.1-cm) pilot extruder and with commercial extrudates. The comparison covered silica-bound, alumina-bound, and self-bound catalysts, as reported in Table 1.

As shown in Table 1, the pore volume, surface area, and crush strength of the extrudates prepared with the HTME extrusion tool (HTME 13 mm, HTME 23 mm) appeared to have similar values with the corresponding properties of the extrudates obtained with the pilot extruder (~2" PILOT) and with those of the commercial extrudates (COMMERCIAL).

Figure 5:
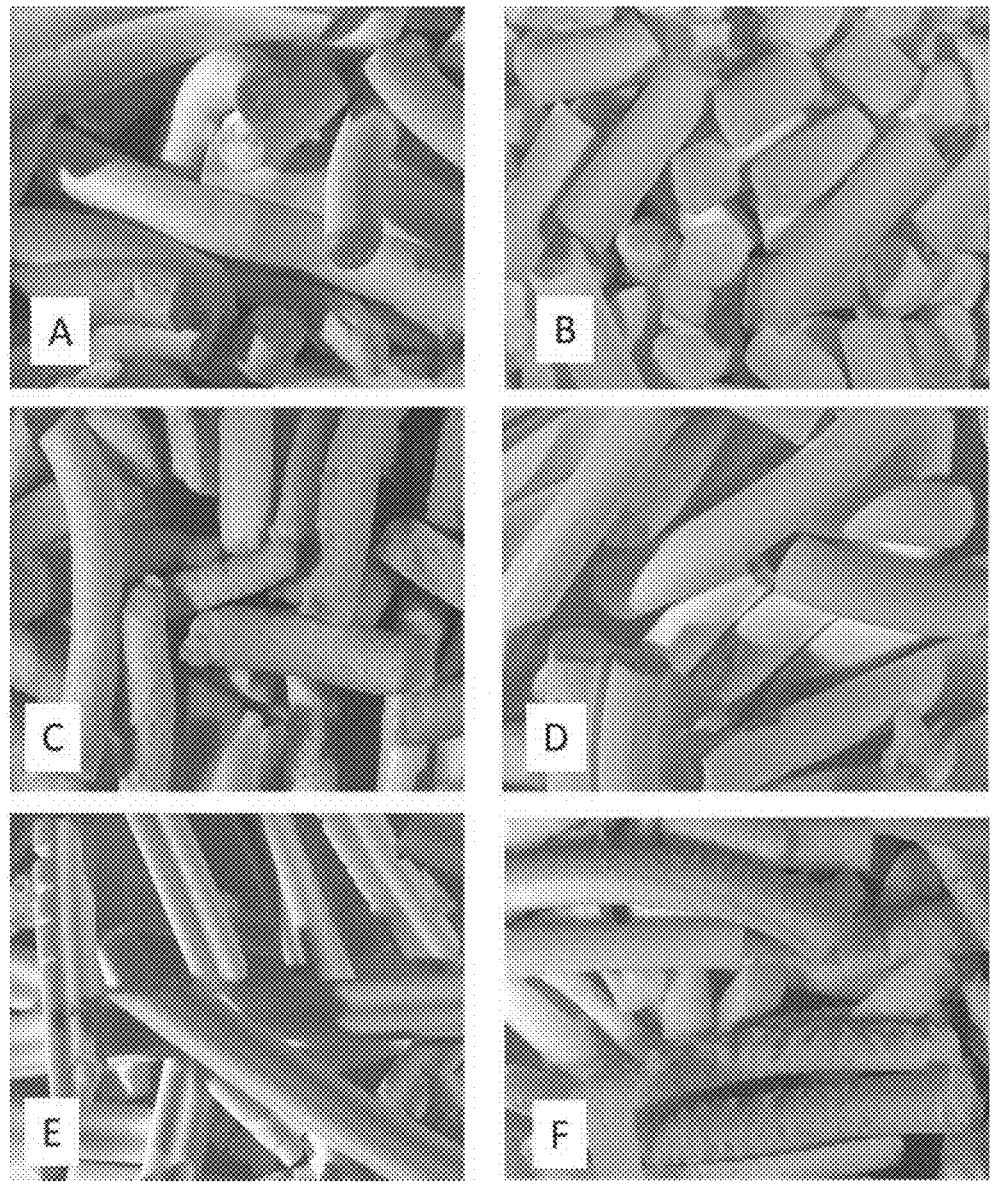
FIG. 5 (views A, B, C, D, E and F) show the pellet morphology of the samples processed according to embodiments of the invention.

FIG. 5 (views A, B, C, D, E and F) shows the pellet morphology of different extrudates prepared with the HTME extruder and with the pilot extruder, as follows: view (A) Si-bound zeolite, HTME 13 mm die; view (B) alumina-bound zeolite, HTME 13 mm die; view (C) self-bound zeolite, HTME 13 mm die; view (D) Si-bound zeolite, ~1/16 inch pilot; view (E) alumina-bound zeolite, ~1/16 inch pilot; view (F) self-bound zeolite, ~1/16 inch pilot.

As shown in FIG. 5, the morphologies of the extrudates prepared with the HTME extruder appeared very similar to the morphologies of extrudates obtained with the pilot extruder, while the later were known to have similar morphology with the industrial scale extrudates.

A SPEX ~31 mm die set was used to build the single extrudate apparatus. The SPEX ~31 mm (~1¼ inch) die set included an evacuable die body, a base, a plunger, two polished steel plates, O-ring vacuum seals, and a knock-out ring for sample disc extraction and had a load limit of ~50 tons. The single extrudate apparatus was built by drilling a ~1.58 mm (~1/16 inch) orifice just above the bottom anvil. A SPEX 3630 X-Press (hydraulic press with ~35-ton up limit) was used for the single extrusion. The press was operated manually to supply pressure to the die set.

To evaluate the single extrudate apparatus performance, extrusions of compositions comprising ~65 parts zeolite/~35 parts alumina ($Al_2O_3$) and ~65 parts zeolite/~35 parts titania ($TiO_2$) were performed. For comparison, the same composition extrusion mixtures were also extruded by using a ~100-gram batch extrusion unit. BET surface area measurements, adsorptions of 2,3-dimethyl butane and n-hexane, Temperature Programmed Ammonia Absorption (TPAA), alpha acidity, pyridine IR, and extrudate crush strength tests were carried out to characterize the extrudates produced by the single extrudate apparatus and the ~100-gram batch extruder.

In the single extrudate apparatus test, about 2 grams of mixture was slowly placed into the SPEX ~31 mm die set. The extrusion mixture was uniformly distributed by using a

TABLE 1

Properties of the HTME, pilot and commercial extrudates.
HIGH THROUGHPUT MULLING AND EXTRUSION RESULTS

| SIZE- SHAPE 1/16" - CYLINDER | MUL- SOLIDS WT % | PORE VOLUME CC/GM | SURFACE AREA M2/GM | CRUSH STRENGTH LBS/INCH |
|---|---|---|---|---|
| SiO2 BOUND | | | | |
| HTME 13 mm | 62 | 0.36 | 347 | 66 |
| HTME 23 mm | 62 | 0.37 | 345 | 56 |
| 2" PILOT | 63 | 0.38 | 338 | 121 |
| COMMERCIAL | 62 | 0.39 | 349 | 92 |

| SIZE- SHAPE 1/16" - QUADRULOBE | MUL-SOLIDS WT % | PORE VOLUME CC/GM | SURFACE AREA M2/GM | CRUSH STRENGTH LBS/INCH |
|---|---|---|---|---|
| ALUMINA BOUND | | | | |
| HTME 13 mm | 56 | 0.49 | 267 | 57 |
| HTME 23 mm | 56 | 0.48 | 263 | 49 |
| 2" PILOT | 57 | 0.44 | 237 | 77 |
| COMMERCIAL | 57 | 0.48 | 203 | 80 |

| SIZE- SHAPE 1/16" - CYLINDER | MUL-SOLIDS WT % | PORE VOLUME CC/GM | SURFACE AREA M2/GM | CRUSH STRENGTH LBS/INCH |
|---|---|---|---|---|
| SELF BOUND | | | | |
| HTME 13 mm | 62 | — | 484 | 52 |
| HTME 23 mm | 62 | — | 480 | 48 |
| 2" PILOT | 57 | 0.53 | 457 | 101 |
| COMMERCIAL | — | 0.58 | 487 | 122 |

Example 2: Single Extrudate Apparatus

Figure 6:
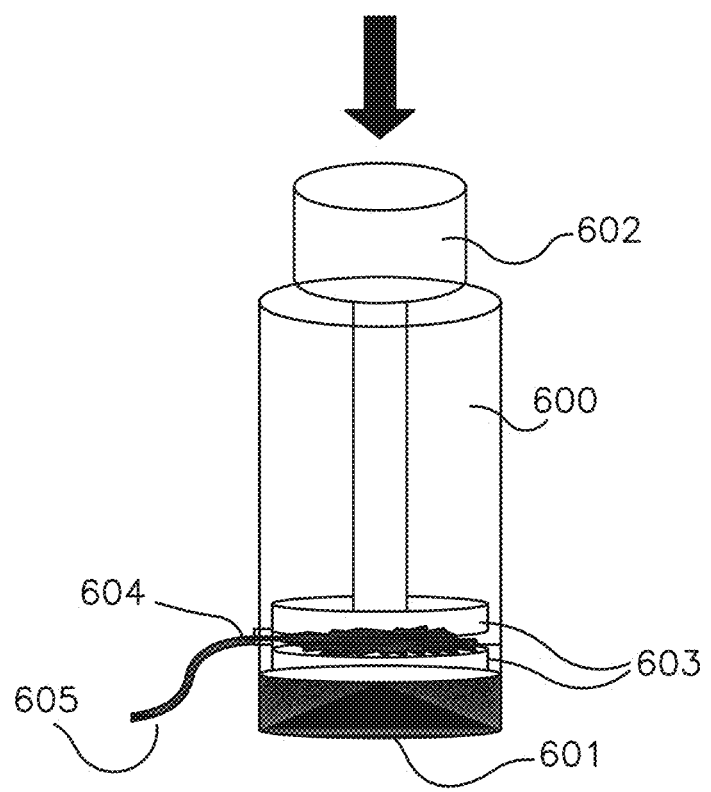
FIG. 6 shows schematically an apparatus for single extrusion configured to be used with the mixing and mulling device.

FIG. 6 shows schematically an apparatus for preparing single extrudates. The single extrudate apparatus in FIG. 6 comprises a die body (600), a base (601), a plunger (602), and two polished steel compression plates (603), as well as a ~1.58-mm (~1/16-inch) orifice (604) just above the base. A hydraulic press was used for the single extrusion. As the pressure increased on the die set, a single extrudate (605) was formed and exited the orifice (604) above the base of the die set.

nickel spatula. The 3630 SPEX press was operated manually to supply pressure to the die set. As the pressure of the press reached about 12 tons, the extrudates of zeolite/$Al_2O_3$ started to come out of the ~1.58 mm (~1/16 inch) orifice. The extrudates broke when their length reached about 5-8 cm (~2-3 inches).

The recovery rate of the extrusion, calculated by the weight of the extrudates collected versus the weight of the extrusion paste loaded in the extruder, was about 30% in the case of the single extrudate apparatus. The recovery rate of the single extrudate apparatus could be improved by decreasing the diameter of the die set piston, by reducing/ minimizing the distance from the orifice to the bottom anvil, and/or by increasing the amount of extrusion feed. For reference, the recovery rate for the ~100-gram batch extrusion was about 67%. Worthwhile to mention, the throughput of the single extrusion was about 6 extrusions per 8-hour day, which was about 3 times that of the ~100-gram batch extrusion.

BET surface areas, pore volumes, $NH_3$ TPAA uptake, and extrudate crush strength results are shown in Table 2. As it can be noticed from Table 2, the basic properties of the extrudates prepared with the single extrudate apparatus (unit) appeared to show similar values as the corresponding properties of the extrudates prepared with the ~100-gram batch extruder. Alumina binder (boehmite) appeared to yield stronger extrudates than titania, as indicated by the higher crush strength results.

TABLE 2

Extrudates prepared with single extrudate apparatus and 100 g batch extrusion unit.

| Extrusion scale comparison | BET ($m^2$/g) | Pore Volume (ml/g) | $NH_3$ TPAA (μmol/g) | Crush Strength (kgf/cm) |
|---|---|---|---|---|
| zeolite (Z) powder | 282 | 0.38 | 0.26 | N/A |
| zeolite/boehmite (65/35), 100 g batch extruder | 324 | 0.56 | 0.38 | 82 |
| zeolite/boehmite (65/35), single extrudate unit | 329 | 0.59 | 0.43 | 63 |
| zeolite/$TiO_2$ (65/35), 100 g batch extruder | 179 | 0.37 | 0.19 | 15 |
| zeolite/$TiO_2$ (65/35), single extrudate unit | 184 | 0.33 | 0.18 | 17 |

The total acidity of the alumina bound zeolite extrudates appeared to be higher than the parent zeolite crystals, as measured by $NH_3$ TPAA, presumably due to the contribution of the Al in boehmite having Lewis acidity.

The concentrations of Brönsted (B Acid) and Lewis (L Acid) acidic sites in pure zeolite (powder) and in extrudates, as determined by pyridine FTIR, were compiled in Table 3. The bands at ~1544 $cm^{-1}$ and the combined bands centered at ~1450 $cm^{-1}$ were chosen for the quantitative evaluation of the Brönsted and Lewis acidic sites of the zeolite extrudates.

As can be seen from Table 3, the Lewis acidity of extrudates appeared to increase with respect to the acidity of pure zeolite. Without wishing to be bound by theory, it seemed that the extrusion processes increased the formation of detrital alumina. The zeolite extrudates bound with alumina or titania also appeared to show less Brönsted acidity than the starting material (zeolite). In conclusion, the extrusion performed with the ~100-gram batch extruder and that performed with the single extrudate unit appeared to lead to similar acidity values.

TABLE 3

Quantitative evaluation of Brönsted and Lewis sites from pyridine FTIR measurements.

| | B Acid (mmol/g) | L Acid (mmol/g) | (B + L) Acid (mmol/g) | Extr vs Z B Acid (mmol/g) | Extr vs Z L Acid (mmol/g) |
|---|---|---|---|---|---|
| zeolite (Z) | 0.17 | 0.06 | 0.23 | 0 | 0 |
| zeolite/$Al_2O_3$ (100 g batch extruder) | 0.07 | 0.12 | 0.19 | −0.04 | 0.08 |
| zeolite/$Al_2O_3$ (single extrudate unit) | 0.09 | 0.13 | 0.22 | −0.02 | 0.09 |
| zeolite/$TiO_2$ (100 g batch extruder) | 0.06 | 0.08 | 0.14 | −0.05 | 0.04 |
| zeolite/$TiO_2$ (single extrudate unit) | 0.08 | 0.06 | 0.14 | −0.03 | 0.02 |

Table 4 shows the adsorption capacities of 2,3-dimethyl butane (23DMB) and n-hexane in zeolite samples. The extrudates prepared in the single extrudate unit and those prepared in the ~100-gram batch extruder appeared to show very similar adsorption capacities.

TABLE 4

Hydrocarbon sorption properties of 2,3 dimethyl butane and n-hexane.

| Extrudate Sorption Property | 23DMB Sorption Capacity (mg/g) | 23DMB Sorption Rate (mg/g/$min^{0.5}$) | N-hexane Sorption Capacity (mg/g) | N-Hexane Sorption Rate (mg/g/$min^{0.5}$) |
|---|---|---|---|---|
| Zeolite | 13 | 30 | 52 | 650 |
| zeolite/$Al_2O_3$ (100 g batch extruder) | 17 | 33 | 43 | 280 |
| zeolite/$Al_2O_3$ (Single extrudate unit) | 17 | 39 | 43 | 230 |

It should be apparent to those skilled in the art that various modifications and/or variations may be made without departing from the scope of the present invention. It is intended that all matter contained in the accompanying specification shall be interpreted as illustrative only and not in a limiting sense. While the present invention has been described in the context of a high throughput experiments for catalyst preparation, the present apparatus and method is not intended to be so limited; rather it is contemplated that the present invention is suitable for mixing and/or mulling samples for chemical and pharmaceutical applications.

What is claimed is:

1. An apparatus for mixing and/or mulling a sample comprising:
   at least one container made of a flexible material, the at least one container being suitable for containing a sample;
   means for holding the at least one container; and
   means for impacting the at least one container,
   wherein the means for holding and the means for impacting are movable relative to each other,
   wherein the means for holding is arranged to rotate and the means for impacting is stationary, or wherein both the means for holding and the means for impacting are arranged to rotate,
   wherein the means for holding, the means for impacting, and the at least one container are arranged such that, when the means for holding and the means for impacting are moving relative to each other, the means for impacting and the at least one container repeatedly collide, whereby an energy of collision is imparted to the sample contained in the at least one container, thereby mixing and/or mulling the sample.

2. The apparatus according to claim 1, wherein arranging the means for holding, the means for impacting, and the at least one container is performed by adapting a dimension and/or a relative position of any of the means for holding, the means for impacting, and the at least one container with respect to each other.

3. The apparatus according to claim 1, wherein the means for impacting is arranged to rotate and the means for holding is stationary.

4. The apparatus according to claim 1, wherein the means for holding comprise at least one disk mounted on a rotatable shaft, the at least one disk comprising a plurality of mounting positions, each mounting position being adapted to hold a container.

5. The apparatus according to claim 1, wherein the means for holding comprise at least one arm mounted on a rotatable shaft, the at least one arm comprising at its unmounted end a mounting position adapted to hold a container.

6. The apparatus according to claim 3, wherein the means for impacting comprise at least one arm mounted on a rotatable shaft.

7. The apparatus according to claim 1, wherein the at least one container is suitable for containing a sample weighing less than 100 grams.

8. The apparatus according to claim 1, wherein the flexible material of the container is impermeable to any liquid contained in and/or formed by the sample.

9. The apparatus according to claim 1, further comprising at least one of means for heating and means for irradiating the at least one container.

10. The apparatus according to claim 1, further comprising means for supplying an additional fluid to an enclosure of the apparatus containing the at least one container.

11. An assembly for performing high throughput experiments comprising:
    an apparatus for mixing and/or mulling a sample according to claim 1; and
    an extruder configured to receive a sample weighing less than 100 grams.

12. The assembly according to claim 11, wherein the extruder is a single extrudate apparatus comprising a die body, a base, a plunger, means for exerting pressure on the sample, and an orifice above the base, configured such that, upon loading the sample and increasing pressure, a single extrudate emanates from the orifice.

13. The assembly according to claim 11, wherein the extruder is a laboratory extrusion tool comprising a plunger, a sample holder, an inner chamber, an extrusion die, and a die holder, configured such that, upon loading the sample and increasing pressure, the sample is extruded through the extrusion die.

* * * * *